(12) United States Patent
Matsunaga et al.

(10) Patent No.: US 10,197,537 B2
(45) Date of Patent: Feb. 5, 2019

(54) NON-DESTRUCTIVE TESTING METHOD AND A NON-DESTRUCTIVE TESTING DEVICE FOR AN ANCHOR BOLT

(71) Applicant: NUCLEAR FUEL INDUSTRIES, LIMITED, Tokyo (JP)

(72) Inventors: Takashi Matsunaga, Osaka (JP); Junji Etoh, Osaka (JP); Yoshihiro Isobe, Osaka (JP)

(73) Assignee: NUCLEAR FUEL INDUSTRIES, LIMITED, Tokyo (JP)

( * ) Notice: Subject to any disclaimer, the term of this patent is extended or adjusted under 35 U.S.C. 154(b) by 0 days.

(21) Appl. No.: 15/329,435

(22) PCT Filed: Jan. 27, 2015

(86) PCT No.: PCT/JP2015/052141
§ 371 (c)(1),
(2) Date: Jan. 26, 2017

(87) PCT Pub. No.: WO2016/017193
PCT Pub. Date: Feb. 4, 2016

(65) Prior Publication Data
US 2017/0227501 A1  Aug. 10, 2017

(30) Foreign Application Priority Data
Aug. 1, 2014  (JP) ................. 2014-157622

(51) Int. Cl.
*G06F 19/00*  (2018.01)
*G01N 29/12*  (2006.01)
(Continued)

(52) U.S. Cl.
CPC .......... *G01N 29/12* (2013.01); *G01N 29/043* (2013.01); *G01N 29/045* (2013.01);
(Continued)

(58) Field of Classification Search
CPC ....... G09B 19/24; B23K 9/0956; B23K 9/093
(Continued)

(56) References Cited

U.S. PATENT DOCUMENTS

| 4,062,229 A | 12/1977 | Godfrey et al. |
| 2009/0056454 A1* | 3/2009 | Turner ............ B61K 9/08 73/600 |

FOREIGN PATENT DOCUMENTS

| JP | 2000-88817 A | 3/2000 |
| JP | 2000-131293 A | 5/2000 |

(Continued)

OTHER PUBLICATIONS

Eto et al., "Daon-ho ni yoru Chemical Anchor no Kenzensei Hyoka Shuho no Kaihatsu (1) Jikkenteki Kento", Atomic Energy Society of Japan Haru no Nenkai Yokoshu (CD-ROM), Mar. 10, 2014 (received date), vol. 2014, p. Rombunno. L43.

(Continued)

Primary Examiner — Edward Raymond
(74) Attorney, Agent, or Firm — Birch, Stewart, Kolasch & Birch LLP

(57) ABSTRACT

This invention provides a method and device for nondestructive testing of an anchor bolt. Said method and device make it possible to quantitatively test the soundness of an anchor bolt affixed to a foundation via an adhesive anchor. In this method for nondestructive testing of an anchor bolt, in which the soundness of an anchor bolt affixed to a foundation via an adhesive anchor is tested, a section of the anchor bolt that is exposed from the surface of the foundation is hit so as to produce an impact noise, a signal waveform corresponding to said impact noise is received and subjected to frequency analysis so as to obtain frequency information for said signal waveform, and the (Continued)

soundness of the anchor bolt is nondestructively, quantitatively tested on the basis of said frequency information.

6 Claims, 4 Drawing Sheets

(51) Int. Cl.
    *G01N 29/04*     (2006.01)
    *G01N 29/44*     (2006.01)
    *G01N 29/46*     (2006.01)

(52) U.S. Cl.
    CPC ......... *G01N 29/4427* (2013.01); *G01N 29/46* (2013.01); *G01N 2291/011* (2013.01); *G01N 2291/015* (2013.01); *G01N 2291/0234* (2013.01); *G01N 2291/0258* (2013.01); *G01N 2291/044* (2013.01); *G01N 2291/101* (2013.01); *G01N 2291/2691* (2013.01)

(58) Field of Classification Search
    USPC .................................... 702/39, 40, 182–185
    See application file for complete search history.

(56) References Cited

FOREIGN PATENT DOCUMENTS

| | | |
|---|---|---|
| JP | 2004-77234 A | 3/2004 |
| JP | 3560830 B2 | 6/2004 |
| JP | 2004-325224 A | 11/2004 |
| JP | 2010-203810 A | 9/2010 |

OTHER PUBLICATIONS

Supplementarly European Search Report dated Jan. 31, 2018 in EP 15827972.9.

\* cited by examiner

[FIG.1]
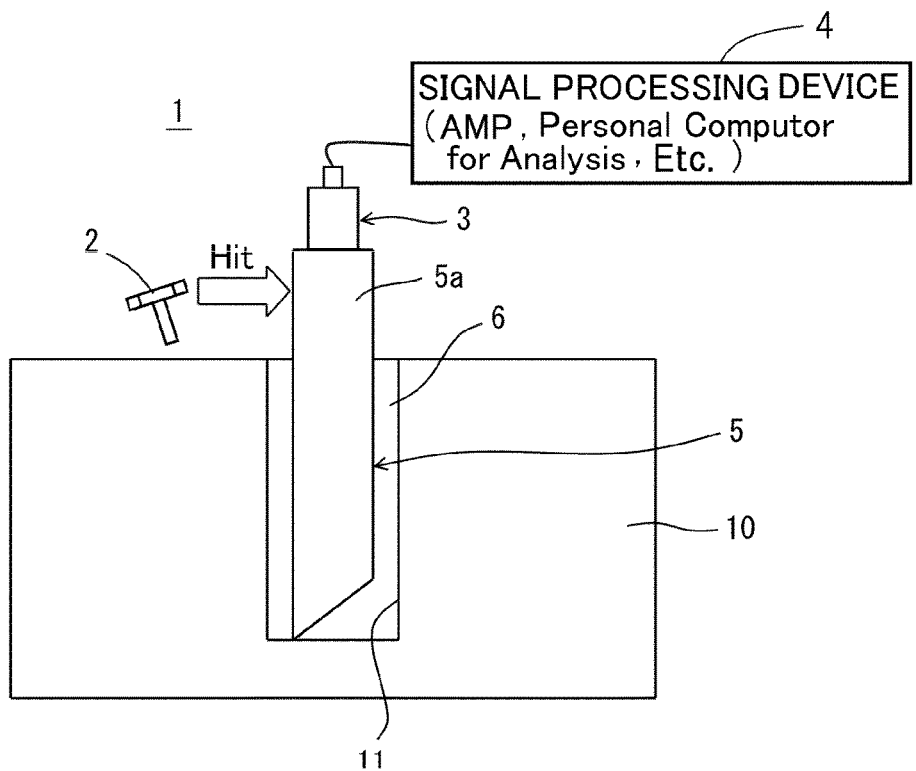
[FIG.2]
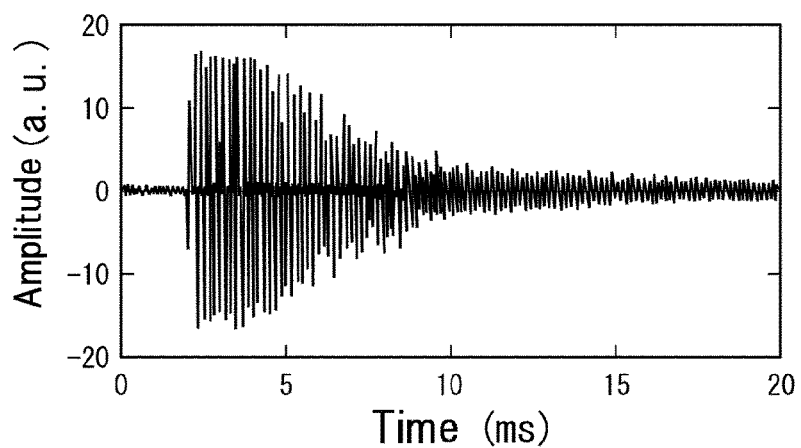

[FIG.3]
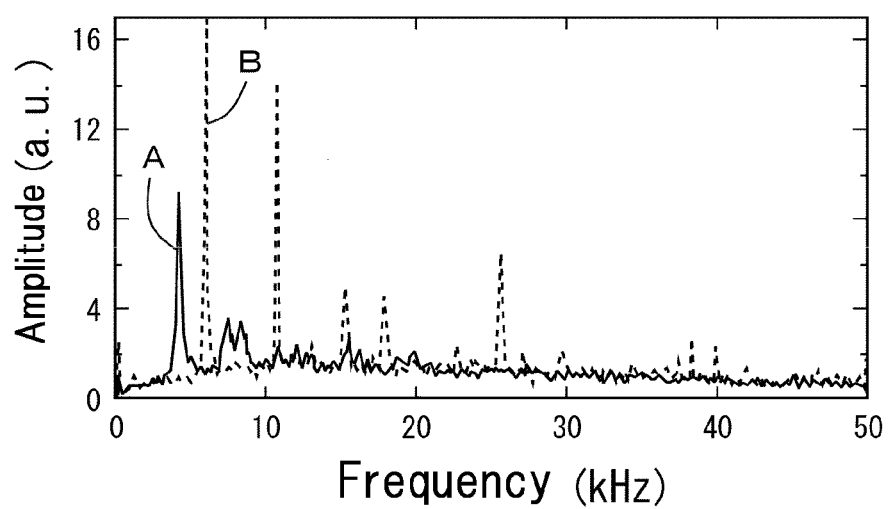

[FIG.4]
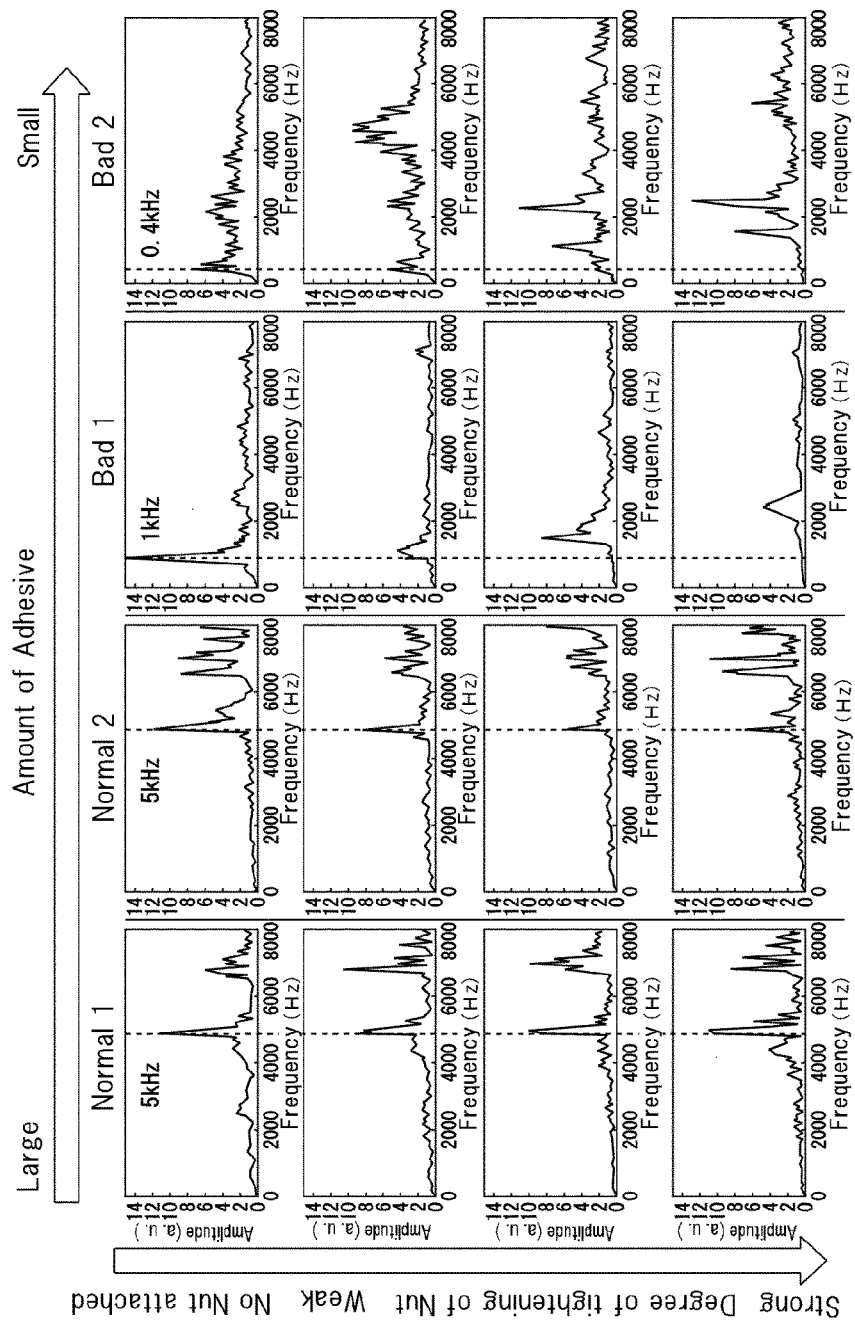

[FIG.5]
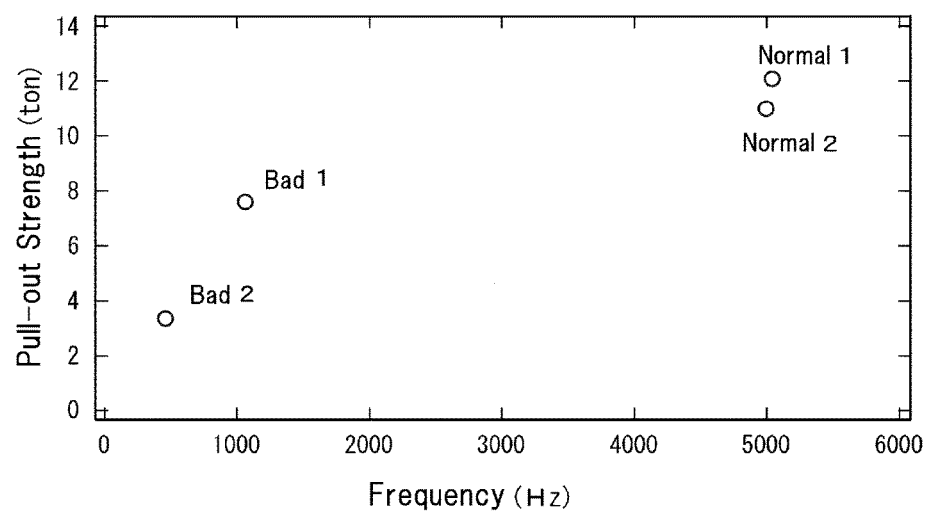

10,197,537 B2

NON-DESTRUCTIVE TESTING METHOD AND A NON-DESTRUCTIVE TESTING DEVICE FOR AN ANCHOR BOLT

FIELD OF THE INVENTION

The present invention relates to a non-destructive testing method and a non-destructive testing device for testing soundness of an anchor bolt fixed to foundation by an adhesive anchor.

Conventionally, adhesive anchors have been used for installing and fixing devices or machines on a foundation of, for example, a concrete structure. Specifically, for example, an adhesive composition of chemical resin is introduced beforehand to a hole opened in a foundation, an anchor bolt is embedded therein, then the chemical resin is set by a chemical reaction, whereby the anchor bolt is physically fastened and fixed in the foundation.

An anchor bolt fixed by such construction methods may be influenced by inappropriate installation, or could suffer aging degradation caused by deterioration or peeling of chemical resin, and when left unattended, these may lead to safety problems of the structure.

Here, inappropriate installation may involve insufficient chemical resin, a deformed bolt (bent or the like), inadequate cleaning of the hole and insufficient stirring, insufficient concrete strength and cracks in concrete. Aging degradation may include a deformed bolt (bent or the like), cracks in the bolt, a bolt breaking, corrosion wastage of the bolt, looseness of a nut, strength deterioration of concrete and cracks of concrete in addition to the deterioration or peeling of chemical resin.

From the viewpoint of ensuring safety of the structure, it has been desired to assess soundness of an anchor bolt and chemical resin (hereinafter generally referred to as "soundness of anchor bolt") of portions embedded in the concrete structure and not visually observable, in a non-destructive manner. For example, the following methods have been adopted.

Impact noise method is a method, in which the head of an anchor bolt exposed from a concrete surface is hit by a hammer, and based on two factors, that is, the sound generated by the hammer at that time and the feeling of impact through the hammer, an inspector determines presence/absence of any abnormality.

Ultrasonic testing is a method, in which an ultrasonic sensor is mounted on the exposed head of an anchor bolt, and based on a reflection signal from the anchor bolt derived from ultrasonic sound applied to the anchor bolt, defects such as corrosion or flaw of the anchor bolt are determined. This method is widely used in general as a non-destructive testing method (For example, Patent Document 1).

Further, a method has been proposed in which an accelerometer is mounted on the exposed head of an anchor bolt, reflected wave of acoustic wave generated by the impact by the hammer is received by the accelerometer, and based on intensity and time lag of the reflected wave, any damage to the anchor bolt, any rupture in the surrounding concrete or the like is tested (For example, Patent Document 2).

PRIOR ART REFERENCES

Patent Documents

[Patent Document 1] JP2004-77234A
[Patent Document 2] JP2010-203810A

SUMMARY OF THE INVENTION

Problems to be Solved by the Invention

Recently, it is desired to quantitatively assess soundness of an anchor bolt in a non-destructive manner with high accuracy. The methods above, however, cannot be considered sufficient from the point of quantitative assessment.

That is, quantitativeness of the impact noise method largely depends on the skill of the inspector, and, therefore, test results are not very reliable and quantitative testing for soundness of anchor bolts with high accuracy has been difficult. Further, depending on the environment of testing (such as noise environment and the status of anchor bolt installation), there is a possibility that the test itself becomes difficult.

The ultrasonic testing allows inspection of soundness of the anchor bolt itself independent of the inspector's skill. It has been difficult, however, to quantitatively assess inappropriate installation or aging degradation.

In the non-destructive testing method disclosed in Patent document 2, oscillation of elastic wave such as ultrasonic wave is caused from the head of the anchor bolt, and based on the intensity and time lag of reflected wave of the elastic wave, soundness of an anchor bolt or concrete is tested. It has been difficult to measure with high accuracy the intensity and time lag of reflected wave of the elastic wave depending on surface roughness of the anchor bolt or a complicated structure of the anchor bolt such as screw cutting. Thus, this method also has the similar problem.

Therefore, an object of the present invention is to provide a non-destructive testing method and a non-destructive testing device enabling quantitative testing of soundness of an anchor bolt fixed in a foundation by an adhesive anchor, in a non-destructive manner.

Means for Solving the Problem

The invention according to claim 1 provides
a non-destructive testing method of testing soundness of an anchor bolt fixed in a foundation by an adhesive anchor, wherein
a portion of said anchor bolt exposed from a surface of said foundation is hit to cause a hitting sound,
a signal waveform of said hitting sound is received and subjected to frequency analysis to obtain frequency information of said signal waveform, and
based on the frequency information of said signal waveform, soundness of said anchor bolt is quantitatively tested in a non-destructive manner.

The invention according to claim 2 provides
the non-destructive testing method of an anchor bolt according to claim 1, wherein
a portion of said anchor bolt exposed from a surface of said foundation is hit to cause a hitting sound,
the signal waveform of said hitting sound is amplified, before the signal waveform of said hitting sound is subjected to frequency analysis, and
the amplified signal waveform of the hitting sound is subjected to Fast Fourier Transform and thereby frequency-analyzed, to obtain the frequency information of said signal waveform.

The invention according to claim 3 provides
the non-destructive testing method of an anchor bolt according to claim 1 or 2, wherein
the frequency information of said signal waveform is compared with database including frequency information of signal waveforms of anchor bolts of which soundness has been confirmed beforehand, whereby soundness of said anchor bolt is quantitatively tested.

The invention according to claim 4 provides the non-destructive testing method of an anchor bolt according to claim 3, wherein said database is compiled as relations between frequency information of signal waveforms and pull-out strength of anchor bolts.

The invention according to claim 5 provides a non-destructive testing device of an anchor bolt for testing soundness of an anchor bolt fixed in a foundation by an adhesive anchor, comprising:

a hitting sound generating means for generating a hitting sound by hitting a portion of said anchor bolt exposed from a surface of said foundation;

a sensor receiving the generated hitting sound;

a signal processing device obtaining a signal waveform of the hitting sound received by said sensor and performing frequency analysis of said signal waveform to obtain frequency information of said signal waveform; and a testing device quantitatively testing soundness of said anchor bolt in a non-destructive manner based on the obtained frequency information of said signal waveform.

The invention according to claim 6 provides the non-destructive testing device of an anchor bolt according to claim 5, wherein said testing device has, as database equipped beforehand, relations between frequency information of signal waveforms and pull-out strength of anchor bolts, and said testing device is configured to evaluate soundness of said anchor bolt by comparing said database with the frequency information of said signal waveform obtained by said signal processing device.

Effect of the Invention

The present invention provides a non-destructive testing method and a non-destructive testing device of an anchor bolt enabling quantitative testing of soundness of an anchor bolt fixed in a foundation by an adhesive anchor, in a non-destructive manner.

BRIEF DESCRIPTION OF THE DRAWINGS

FIG. 1 A schematic illustration showing a non-destructive testing device of an anchor bolt in accordance with an embodiment of the present invention FIG. 2 A graph showing an example of signal waveform of the hitting sound received by the sensor FIG. 3 A graph showing an example of frequency information of the signal waveform obtained from frequency analysis by a signal processing device FIG. 4 A graph showing the frequency information of the signal waveform about anchor bolts to be tested FIG. 5 A graph showing relations between frequency information of signal waveforms and pull-out strength about anchor bolts to be tested

EMBODIMENTS OF CARRYING OUT THE INVENTION

Referring to the figures, a non-destructive testing method and a non-destructive testing device of an anchor bolt regarding an embodiment of the present invention will be described below.

1. Non-Destructive Testing Device

FIG. 1 is a schematic illustration showing a non-destructive anchor bolt testing device in accordance with the embodiment, which includes an impact hammer 2, a sensor 3, and a signal processing device 4. An anchor bolt 5 is inserted to a hole opened in a foundation 10 of a concrete structure and fixed in foundation 10 with chemical resin 6.

(1) Impact Hammer

Impact hammer 2 is the hitting sound generating means for generating a hitting sound inside anchor bolt 5 by hitting a head portion 5a of anchor bolt 5 exposed from the surface of foundation 10. Impact hammer 2 is not specifically limited and a general, commercially available hammer may be used.

(2) Sensor

Sensor 3 is mounted in contact with anchor bolt 5, on an upper surface of head portion 5a of anchor bolt 5, and it receives a signal waveform of the hitting sound generated by the hitting by impact hammer 2. The hitting sound received by sensor 3 is thereafter transmitted to signal processing device 4. As sensor 3, mainly, an AE sensor as a piezoelectric element sensor receiving high frequency component in ultrasonic range (several tens kHz to several MHz) is used. It is not limiting, however, and a general sonic sensor may be used.

(3) Signal Processing Device

Signal processing device 4 is mounted for obtaining the signal waveform of the hitting sound received by sensor 3, performing frequency analysis and thereby obtaining frequency information of the signal waveform. It includes a signal amplifier (amp) for amplifying the signal waveform of the hitting sound transmitted from sensor 3, and a personal computer for analysis, performing frequency analysis of the amplified signal waveform of the hitting sound.

The personal computer for analysis includes signal processing software for analyzing the signal waveform of hitting sound, and by performing frequency analysis such as FFT (Fast Fourier Transform) on the signal waveform of the hitting sound received by sensor 3, frequency information of the signal waveform can be obtained.

Further, frequency information of signal waveforms of anchor bolts, of which soundness has been confirmed beforehand, is obtained in advance through, for example, a mock-up test, and stored as database in a storage unit of the personal computer for analysis (Not shown in the drawing).

2. Non-Destructive Testing Method

Next, the non-destructive testing method of quantitatively testing, in a non-destructive manner, soundness of an anchor bolt (soundness of an anchor bolt and chemical resin) fixed in the foundation by an adhesive anchor, using the non-destructive testing device 1 will be described.

First, head portion 5a of anchor bolt 5 embedded with the head portion 5a exposed from the surface of foundation 10 is hit by impact hammer 2, and whereby a hitting sound is generated in anchor bolt 5.

The generated hitting sound is received by sensor 3 and transmitted to signal processing device 4, by which a signal waveform of the hitting sound is obtained. FIG. 2 shows an example of the obtained signal waveform of the hitting sound. As can be seen from FIG. 2, the signal waveform of the hitting sound generates by the impact of impact hammer 2, and attenuates gradually as time passes.

Then, the signal waveform of said hitting sound is amplified by the signal amplifier of signal processing device 4. Thereafter, the amplified signal waveform of the hitting sound is subjected to FFT using signal processing software installed in the personal computer for analysis of signal processing device 4 and thus frequency-analyzed, whereby frequency information of the signal waveform is obtained. FIG. 3 shows an example of the obtained frequency information of the signal waveform.

In FIG. 3, "A" shows frequency information in the case the anchor bolt is coated with a chemical resin, and "B" shows frequency information in the case the anchor bolt is not coated with a chemical resin.

As can be seen from FIG. 3, frequencies at which a peak appears and peak heights are different in A and B. Therefore, it is possible to quantitatively assess and test the state of chemical resin coating on the anchor bolt, that is, soundness of the anchor bolt, by knowing the frequency at which a peak appears and the peak height.

Here, it is preferred that, as in the present embodiment, the obtained frequency information can be compared with pre-stored database, since it enables quantitative testing of the soundness of an anchor bolt in a shorter time with higher accuracy.

Specifically, if relations between frequency information of the signal waveform and physical properties as an indicator of soundness of anchor bolts are stored in advance as database, the soundness of the anchor bolt can be evaluated by comparing the frequency information of the signal waveform obtained this time by signal processing device 4 with the database. As the physical property used as the indicator, pull-out strength is particularly preferable. If the relations between the frequency information of signal waveforms and the pull-out strength of anchor bolts are compiled as database, soundness of the anchor bolt can easily be evaluated based on the pull-out strength of the anchor bolt.

3. Effects of the Embodiment

According to the present embodiment, based on the frequency information of the signal waveform obtained by frequency analysis of the signal waveform of the hitting sound, soundness of a portion, that cannot directly be observed visually, of the anchor bolt fixed in a foundation by an adhesive anchor can quantitatively tested in a non-destructive manner.

Specifically, the non-destructive testing device in accordance with the present embodiment aims at quantitative testing soundness of an adhesive anchor in a non-destructive manner. In an adhesive anchor, a chemical resin adheres around the anchor bolt and signal waveform of the hitting sound allowing appropriate frequency analysis can be obtained. Further, since the frequency information obtained from the signal waveform of hitting sound changes reflecting degree of adhesion of chemical resin, deterioration of the chemical resin and surrounding concrete strength, etc., it is possible to quantitatively test soundness in a non-destructive manner by using the non-destructive testing device in accordance with the present embodiment.

Further, the frequency information used as the index in the non-destructive testing device of the present embodiment is obtained from the hitting sound derived from eigen frequency of the structure such as the anchor bolt, resin or concrete. Therefore, by the comparison with the database, soundness of even a complicated structure can easily be tested.

Intensity of peak frequency of the frequency information depends, for example, on surface roughness of the anchor bolt. The peak frequency and the intensity ratio of peak frequency, however, do not much depend on the surface roughness. Therefore, different from the reflection wave of an elastic wave, these are independent of the surface roughness of the object to be measured. Thus, highly accurate testing of soundness is possible.

Further, in general, when a device, machine or the like is to be fixed on a foundation such as a concrete structure, it is often the case that the device or machine is connected to an anchor bolt with a nut or a base plate interposed. According to the present embodiment, it is possible to test soundness of the anchor bolt in a non-destructive manner without necessitating removal of such a nut or a base plate.

EXAMPLES

Example 1

First, to a foundation having holes of a prescribed size opened, chemical resin was inserted and thereafter, to each hole, an M16 steel anchor bolt was inserted, and thus, the foundation and the anchor bolts were fastened. Here, two samples (Normal 1, 2) with sufficient amount 100% of chemical resin as sound samples, and two unsound samples, one with 50% of chemical resin (Bad 1) and one with 35% of chemical resin (Bad 2) were prepared.

TABLE 1

|  | Amount of Chemical Resin (%) |
| --- | --- |
| Normal 1 | 100 |
| Normal 2 | 100 |
| Bad 1 | 50 |
| Bad 2 | 35 |

2. Evaluation Method

Using the above-described non-destructive testing method, frequency information of the four samples of anchor bolt was obtained. At the time of measurement, first, each anchor bolt was tested before attaching a nut, and thereafter, the nut was gradually tightened and the frequency information at various degree of tightening was obtained. The results are as shown in FIG. 4.

3. Test Results

It can be seen from FIG. 4 that when the anchor bolt did not have a nut attached to its upper portion, the peak frequency of the frequency information shifted to the low frequency side as the amount of chemical resin decreased.

When the anchor bolt had a nut attached to its upper portion, the frequency at which peak appeared was unchanged even when the degree of tightening of the nut was changed, in anchor bolts (Normal 1, Normal 2) having sufficient amount of chemical resin. On the other hand, in anchor bolts (Bad 1, Bad 2) having smaller amount of chemical resin, the frequency at which peak appeared shifted to the high frequency side as the degree of tightening of the nut increased.

Example 2

Next, focusing on the point that inappropriate installation or aging degradation lowers pull-out strength of an anchor bolt, correlation between the frequency information and the pull-out strength was calculated, and experiments were performed to evaluate possibility of testing soundness of an anchor bolt based on the correlation.

1. Preparation of Samples for Example 2

In the same way as in Example 1, to a foundation having holes of a prescribed size opened, chemical resin was inserted to each hole at the amounts shown in Table 1, an M16 steel anchor bolt was inserted, and thus, the foundation and the anchor bolts were fastened. Thus, two samples (Normal 1, Normal 2) as sound samples, and two unsound examples (Bad 1, Bad 2) were prepared.

2. Evaluation Method

For each anchor bolt, Normal 1, Normal 2 and Bad 1, Bad 2, pull-out strength was measured, and the frequency information was obtained using the above-described non-destructive testing method. The results are as shown in FIG. 5.

3. Test Results

It can be seen from FIG. 5 that when the pull-out strength of anchor bolt is low, the frequency information shifted to the low-frequency side, and when the pull-out strength of anchor bolt is high, the frequency information shifted to the high-frequency side. Therefore, if this relation is compiled beforehand as database, it is possible to easily know the pull-out strength of an anchor bolt and evaluate soundness from the frequency information.

It can be seen from the results in Example 1 and Example 2 that soundness of an anchor bolt fixed in a foundation by an adhesive anchor can be tested quantitatively in a non-destructive manner by obtaining the frequency information using said non-destructive testing device and said non-destructive testing method.

The present invention has been described above with reference to the embodiments. However, the present invention is not limited to said embodiments. Various changes may be made on said embodiments within the scope identical or equivalent to that of the present invention.

DESCRIPTION OF THE REFERENCE NUMERALS

1 Non-destructive testing device
2 impact hammer
3 sensor
4 signal processing device
5 anchor bolt
5*a* head portion of anchor bolt
6 chemical resin
10 foundation
11 hole

What is claimed is:

1. A non-destructive testing method of testing soundness of an anchor bolt fixed in a foundation by an adhesive anchor, wherein
   a portion of said anchor bolt exposed from a surface of said foundation is hit to cause a hitting sound,
   a signal waveform of said hitting sound is received and subjected to frequency analysis to obtain frequency information of said signal waveform, and
   based on the frequency information of said signal waveform, soundness of said anchor bolt is quantitatively tested in a non-destructive manner.

2. The non-destructive testing method of an anchor bolt according to claim 1, wherein
   the signal waveform of said hitting sound is amplified, before the signal waveform of said hitting sound is subjected to frequency analysis, and
   the amplified signal waveform of the hitting sound is subjected to Fast Fourier Transform and thereby frequency-analyzed, to obtain the frequency information of said signal waveform.

3. The non-destructive testing method of an anchor bolt according to claim 1, wherein
   the frequency information of said signal waveform is compared with database including frequency information of signal waveforms of anchor bolts of which soundness has been confirmed beforehand, whereby soundness of said anchor bolt is quantitatively tested.

4. The non-destructive testing method of an anchor bolt according to claim 3, wherein
   said database is compiled as relations between frequency information of signal waveforms and pull-out strength of anchor bolts.

5. A non-destructive testing device of an anchor bolt for testing soundness of an anchor bolt fixed in a foundation by an adhesive anchor, comprising:
   a hitting sound generating means for generating a hitting sound by hitting a portion of said anchor bolt exposed from a surface of said foundation;
   a sensor receiving the generated hitting sound;
   a signal processing device obtaining a signal waveform of the hitting sound received by said sensor and performing frequency analysis of said signal waveform to obtain frequency information of said signal waveform; and
   a testing device quantitatively testing soundness of said anchor bolt in a non-destructive manner based on the obtained frequency information of said signal waveform.

6. The non-destructive testing device of an anchor bolt according to claim 5, wherein
   said testing device has, as database equipped beforehand, relations between frequency information of signal waveforms and pull-out strength of anchor bolts, and
   said testing device is configured to evaluate soundness of said anchor bolt by comparing said database with the frequency information of said signal waveform obtained by said signal processing device.

* * * * *